United States Patent [19]

Schwartz

[11] Patent Number: 4,472,253

[45] Date of Patent: Sep. 18, 1984

[54] PROCESS FOR THE PREPARATION OF AN N-SUBSTITUTED 3-O-ALKYL-14-HYDROXYNORMORPHINONE DERIVATIVE

[75] Inventor: Martin A. Schwartz, Tallahassee, Fla.

[73] Assignee: The Florida Board of Regents on behalf of the Florida State University, Tallahassee, Fla.

[21] Appl. No.: 293,461

[22] Filed: Aug. 17, 1981

[51] Int. Cl.³ .................... B01J 19/12; C07D 491/00
[52] U.S. Cl. .................................. 204/158 R; 546/45
[58] Field of Search ................. 204/158 N; 546/44–45

[56] References Cited

U.S. PATENT DOCUMENTS 2,772,270  11/1956  Weiss .................................... 546/45
4,001,249   1/1977  Noyori et al. .................. 204/158 R

OTHER PUBLICATIONS

Bentley, The Chemistry of the Morphine Alkaloids, (1954), pp. 251, 252 & 262.

Primary Examiner—Howard S. Williams
Attorney, Agent, or Firm—Senniger, Powers, Leavitt and Roedel

[57] ABSTRACT

A 14-hydroxy group is introduced into a morphinan structure by singlet oxygen reaction with a novel dienol ester of an N-substituted-3-O-alkylnormorphinone. carry out the singlet oxygen reaction, the enolate substrate may be contacted with molecular oxygen in the presence of light and a light sensitizing agent or in the presence of a chemical reagent for forming singlet oxygen from molecular oxygen.

10 Claims, No Drawings

PROCESS FOR THE PREPARATION OF AN N-SUBSTITUTED 3-O-ALKYL-14-HYDROXYNORMORPHINONE DERIVATIVE

BACKGROUND OF THE INVENTION

This invention relates to the field of synthesis of 14-hydroxymorphinans and more particularly to a novel and improved process for the preparation of noroxycodone, noroxymorphone and certain novel intermediates useful in such synthesis.

14-hydroxymorphinans, such as naloxone, naltrexone, and nalbuphine are important morphine derivatives due to their behavior as potent analgesics and/or narcotic antagonists. Prior to the instant invention, the most practical synthetic routes to the preparation of these pharmaceuticals have utilized thebaine as a starting material. Thus, in accordance with one conventional process, thebaine is oxidized to 14-hydroxycodeinone by use of m-chloroperbenozoic acid in an acetic acid/trifluoroacetic acid mixture or by a mixture of hydrogen peroxide and formic acid. 14-hydroxycodeinone is catalytically reduced to oxycodone that is in turn O-demethylated with boron tribromide to yield oxymorphone. After blocking of the hydroxyl groups with a suitable blocking agents such as acetyl groups, the oxymorphone derivative is reacted with cyanogen bromide to yield an N-cyanodihydronormorphinone derivative that is thereafter hydrolyzed to 14-hydroxydihydronormorphinone (noroxymorphone). Although the synthesis is effective, the availability of thebaine is limited and its cost high, thereby contributing to high cost of the noroxymorphone and the 14-hydroxymorphinans derived from it.

Because of the scarcity and high cost of thebaine, efforts have been made in the art to devise new methods for the synthesis of noroxymorphone and noroxycodone.

Because of their relatively low price and abundance, codeine and other 3-O-alkylmorphines are attractive and readily available potential precursors to noroxymorphone. The key transformation required for conversion of codeine to noroxymorphone is oxidation at the allylic position to provide the 14-hydroxy derivative. However, the direct allylic oxidation of codeine has met with only limited success and has generally been characterized by low yields. Thus, for example, attempts have been made to introduce the 14-hydroxy group by oxidation with chromic anhydride and sulfuric acid, with manganese dioxide, with selenium dioxide, and with t-butyl hydroperoxide. None of these efforts have produced 14-hydroxylated products in satisfactory yields. Other attempts have been made to synthesize thebaine from codeine or codeinone, thereby reducing the scarcity and cost of that intermediate, from which the 14-hydroxy compounds can be produced by known methods with relative efficiency.

There has, however, remained, an unfulfilled need in the art for novel and efficient methods for preparing noroxycodone and noroxymorphone from codeine.

SUMMARY OF THE INVENTION

Among several objects of the invention, therefore, may be noted the provision of a novel method for producing noroxycodone and noroxymorphone; the provision of such a method which utilizes a relatively abundant raw material, such as codeine; the provision of such a method by which the 14-hydroxymorphinan precursors can be economically produced; the provision of such a method by which such precursors can be produced in high yield; the provision of such method which can be carried out in a relatively straightforward manner without elaborate separations; the provision of such a method that is subject to effective and routine process control; and the provision of such a method which can be reliably operated to produce noroxycodone and noroxymorphone of high quality.

It is the further object of the present invention to provide certain novel intermediates useful in the synthesis of noroxycodone and noroxymorphone and to provide methods for the preparation of such intermediates.

Briefly, therefore, the present invention is directed to a novel process for producing an N-substituted 3-O-alkylnormorphinone enolate having the structural formula

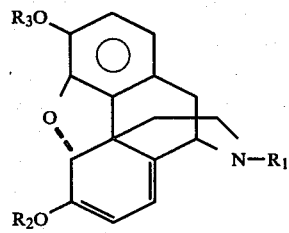

where $R_1$ is

or cyano and $R_{11}$ may be an aliphatic, aryl, oxyaliphatic or aryloxy substituent; $R_2$ is an acyl group and $R_3$ is a lower alkyl group. The process comprises reacting an N-substituted-3-O-alkylnormorphinone derivative having the structural formula

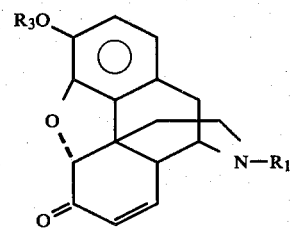

where $R_1$ and $R_3$ are as defined above with an acid anhydride having the formula

or an acyl halide having the formula

where X is an halogen and $R_2$ is as defined above, in the presence of a base.

The invention is further directed to the process for producing an N-substituted-3-O-alkyl-14-hydroxynormorphinone derivative having the structural formula where $R_1$ and $R_3$ are as defined above. In accordance with this method, an N-substituted-3-O-alkyl normorphinone enolate substrate is contacted and reacted with singlet oxygen. The enolate has the structural formula

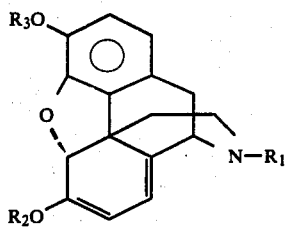

where $R_1$, $R_2$, and $R_3$ are as defined as above.

Also included in the invention is a process for producing an N-substituted-3-O-alkylnoroxymorphone derivative having a structural formula

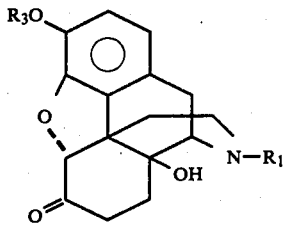

where $R_1$ and $R_3$ are as defined above. The process comprises catalytic hydrogenation of an N-substituted-3-O-alkyl-14-hydroxynormorphinone derivative having a structural formula

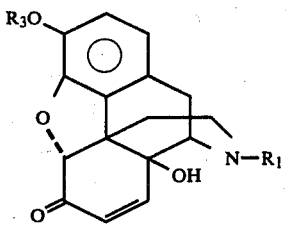

Further included in the invention is a process for producing a 3-O-alkylnoroxymorphone having the structural formula

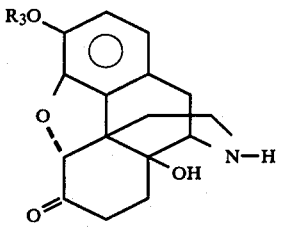

where $R_3$ is lower alkyl. In this process, an N-substituted-3-O-alkylnoroxymorphone derivative having the structural formula

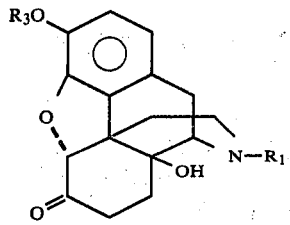

where $R_1$ and $R_3$ are as defined above, is hydrolyzed by contacting it with an acid in the presence of water.

The invention is further directed to a process for producing noroxymorphone. In this process, an N-substituted-3-O-alkylnoroxymorphone derivative having the structural formula

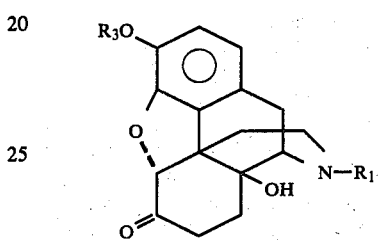

where $R_1$ and $R_3$ are as defined above, is reacted with an acid selected from the group consisting of boron tribromide and pyridinium chloride to produce an N-substituted noroxymorphone derivative having the structural formula

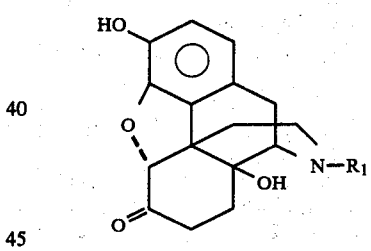

where $R_1$ is as defined above. The noroxymorphone derivative is thereafter hydrolyzed with an acid in the presence of water to produce noroxymorphone.

The invention is further directed to a novel compound having the structural formula

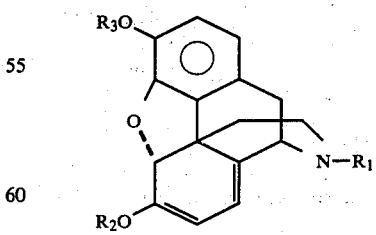

where $R_1$ is

or cyano, $R_{11}$ is aliphatic, aryl, oxyaliphatic or aryloxy, $R_2$ is acyl and $R_3$ is lower alkyl.

Further included in the invention is a compound having the structural formula

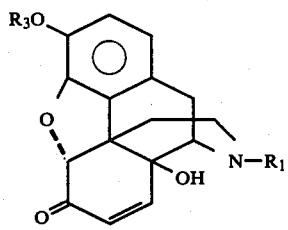

where $R_1$ and $R_3$ are as defined above.

Also included in the invention is the compound having the structural formula

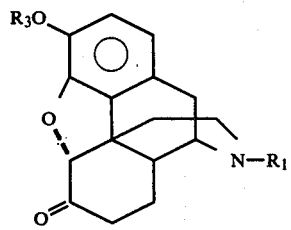

where $R_1$ and $R_3$ are as defined above.

Other objects and features will be in part apparent and in part pointed out hereinafter.

DESCRIPTION OF THE PREFERRED EMBODIMENTS

In accordance with the present invention, a novel, economical and efficient method has been discovered for producing noroxycodone and noroxymorphone using codeine and related 3-O-alkyl derivatives of morphine as a starting material. Thus, a novel and advantageous route is provided for the synthesis of various 14-hydroxymorphinans such as naloxone, naltrexone, and nalbuphine. The method of the invention also provides certain novel intermediates useful in the synthesis of other products as well as novel methods for the preparation of such intermediates.

The efficiency and advantages of the method of the invention are made possible by the combination of several essential novel concepts and techniques. These include N-demethylation of codeine or a codeine analog starting material prior to the oxidation thereof; blocking of the amine group by substitution of a cyano group or conversion to an amide; and introduction of the 14-hydroxyl group by oxidation of an enolate of an N-substituted norcodeinone or other N-substituted 3-O-alkyl-morphinone by singlet oxygen generated chemically or by the impingement of light. Such synthesis route affords high yields, good reliability, and straightforward operation and control at each and every step of the synthesis. High overall yields are obtained in the conversion of codeine to noroxymorphone and noroxycodone and a major reduction in the cost of synthesis of 14-hydroxymorphinans is achieved by comparison with those processes which utilize thebaine as a starting material.

Although the primary purpose and function of the invention is the conversion of a raw material such as codeine to noroxymorphone, novel intermediates are produced in the course of the overall synthesis and particular novel methods are provided both for the preparation of the novel intermediates and for noroxycodone. Certain other intermediates are known compounds which may be prepared by art-recognized methods other than those specifically disclosed herein. Optionally, the desired products can be prepared using any of the various intermediates as the starting material.

Preferably, however, the starting material is codeine or another 3-O-alkylmorphine such as ethyl morphine (3-O-ethylmorphine) or propyl morphine (3-O-propylmorphine). Generally, the initial starting material has the structural formula

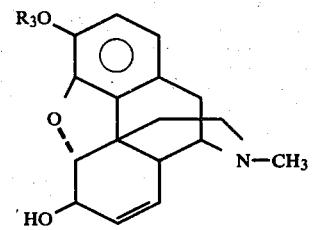 (Formula I)

wherein $R_3$ is lower alkyl. Where $R_3$ is methyl, the starting material is codeine which is a natural constituent of opium. However, both codeine and its higher alkyl analogs are readily derived by alkylation of morphine which is the principal component of opium extracts.

In the initial step of the synthesis, codeine or other starting material of Formula I is N-demethylated to produce an N-substituted-3-O-alkylnormorphine having the structural formula

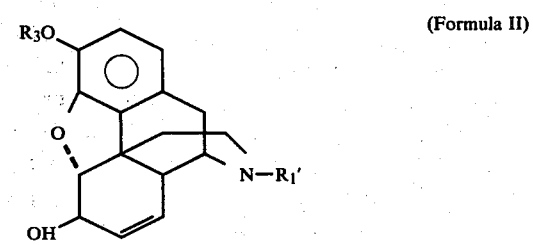 (Formula II)

where $R_1'$ is cyano or

and $R_{12}$ is oxyaliphatic or aryloxy. Thus, for example, $R_{12}$ may be methoxy, ethoxy, propoxy, heptoxy, phenoxy, butenoxy, benzyloxy, or naphthyloxy. N-demethylation is carried out by reacting the compound of Formula I with a cyanogen halide or a haloformate ester having the formula

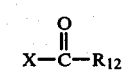

where X is a halogen, preferably bromine or chlorine. The N-demethylation reaction is promoted by the presence of a weak base such as potassium bicarbonate or sodium acetate and is conducted in an appropriate solvent such as chloroform, dichloroethane, dioxane, toluene, benzene or other halogenated or aromatic solvents. This is a known reaction which readily takes place at atmospheric pressure and moderate temperature, for example, 50°–100° C., within a period of several hours. Preferably an excess of the demethylation reagent is used together with approximately an equivalent of the weak base per equivalent of the substrate of Formula I. If desired, the product N-substituted-3-O-alkylnormorphine can be recovered by washing the reaction solution, drying and evaporating the solvent. Alternatively, the next step of the synthesis can be carried out without a recovery step.

In the next step of the synthesis, the N-substituted-3-O-alkylnormorphine is oxidized to produce an N-substituted-3-O-alkylnormorphinone having the structural formula

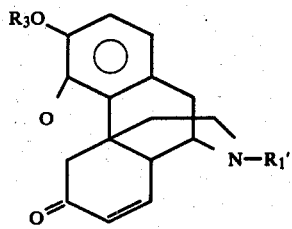

(Formula III)

where $R_1'$ and $R_3$ are as defined above. This is also a known reaction can be carried out in good yield with any of a variety of common alcohol oxidizing agents. Advantageously, manganese dioxide is used as the oxidizing agent and is slurried in a solution of the N-substituted-3-O-alkylnormorphine, for example, the reaction solution produced in the N-demethylation step. The oxidation reaction is preferably conducted at a temperature of 0°–50° C., most conveniently and effectively at room temperature. The normorphinone product can be recovered by conventional methods, for example, filtration of the reaction solution and evaporation of the solvent.

A dienol ester is next prepared by reaction of the the compound of Formula III with an acid anhydride of the formula (R$_2$)$_2$O or an acyl halide

R$_2$—X where X is halogen and $R_2$ is an acyl group. Alternatively, this step of the synthesis can be carried out by reaction of the anhydride or acyl halide with an N-acyl-3-O-alkylnormorphinone. Generally, therefore, this step involves the preparation of an enolate ester of an N-substituted-3-O-alkylnormorphinone having the structural formula

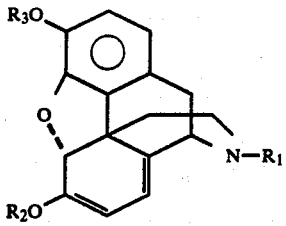

(Formula IV)

where $R_2$ and $R_3$ are as defined above, $R_1$ is cyano or

and $R_{11}$ is aliphatic, oxyaliphatic, aryl or aryloxy, by reaction of the aforesaid acid anhydride or acyl halide with a compound having the structural formula

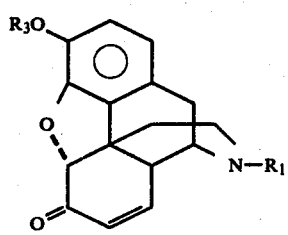

(Formula IIIa)

The compounds of Formula IV are novel intermediates useful in the synthesis of noroxycodone and noroxymorphone and other intermediates.

In the preparation of the novel enolate, a preferred reagent is acetic anhydride, but acetyl chloride, propionic anhydride, propanoyl bromide, benzoic anhydride, benzoyl chloride and other common anhydrides and acid halides may also be used. An excess of acylating agent is used, typically 1 to 10 equivalents per equivalent of Formula IIIa substrate. Reaction may take place in any conventional inert solvent, including those used in the N-demethylation and normorphine oxidation reactions. In the case of acetylation, however, the acetic anhydride itself preferably constitutes the reaction medium. A base such as sodium acetate, pyridine, triethylamine or other tertiary amine promotes or catalyzes the reaction. Amines are the catalysts of choice where an acyl halide reagent is used. Where an anhydride is employed, the salt of a weak acid is preferred, most preferably a salt of the same acid from which the anhydride is derived. Reaction is preferably conducted at a temperature in the range of 80°–100° C., though this range is not generally critical. Where the reaction takes place in an acid anhydride medium, it is conveniently carried out under atmospheric reflux conditions. Excessively long reaction times can cause some lowering of yields and the optimum reaction time varies inversely with the temperature. For example, for acetylation in an acetic anhydride medium containing 10 parts by weight N-ethoxycarbonylnorcodeinone and one part by weight sodium acetate, reaction is preferably terminated after about 1.5 hours at atmospheric reflux.

In the next step of the synthesis, an enolate substrate having the structure of Formula IV is reacted with singlet oxygen to substitute a hydroxyl group in the 14 position and oxidize the enolate structure to a normorphinone structure, thus yielding an N-substituted-3-O-alkyl-14-hydroxynomorphinone having the structural formula:

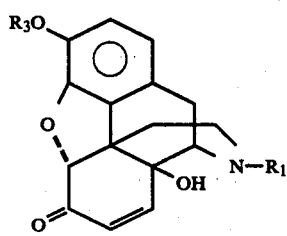

(Formula V)

The compounds of Formula V are also novel intermediates.

Oxidation of the enolate is preferably effected by contacting the enolate substrate with oxygen in the presence of a sensitizing agent effective for forming singlet oxygen from molecular oxygen in the presence of light. Preferred sensitizers include rose bengal (alkali metal salt of 4,5,6,7-tetrachloro-2',4',5',7' tetraiodofluorescein) and methylene blue (3,7-bis (dimethylamino) phenothiazin-5-ium chloride), the latter being most preferred from the standpoint of process economics. Other useful sensitizers include eosin, erythrosin, chlorophyll A, chlorophyll B, hematoporphyrin and zinc tetraphenylporphin. Each of these catalyzes formation of singlet oxygen in the presence of visible light. Preferably, a solution is prepared containing the sensitizer and compound of Formula IV in a solvent therefor, preferably a halogenated hydrocarbon or mixture thereof with a primary alcohol. Aromatics, ketones and carbon bisulfide may also be used as solvents. The solution is then contacted with oxygen and irradiated with light, whereupon the oxidation reaction proceeds rapidly at moderate temperature. Contact is advantageously accomplished by bubbling a stream of pure molecular oxygen through the solution, but air may also be used as an oxygen source. It is also preferred that the reaction mixture be maintained at a temperature below room temperature, generally in the range of $-20°$ to $+25°$ C., to avoid decomposition of intermediates formed in the course of the reaction. Proportions of the components of the reactant solution are not critical but typically the reaction solution may contain $10^{-4}$ to $10^{-3}$ moles/liter of the sensitizer. After reaction is complete, typically in 6 to 24 hours, thiourea is added to the reaction solution to quench peroxides contained therein. The product of Formula V may be recovered by conventional solvent evaporation and washing steps. Although synthesis can optionally proceed from codeine or other 3-O-alkylmorphine starting material through the formation of the product of Formula V without recovery of any of the products of Formula I-IV, it is important to isolate the product of Formula V from the methylene blue or other sensitizer before proceeding with the subsequent steps of the synthesis of noroxycodone or noroxymorphone.

Alternatively oxidation of the enolate may be carried out with chemically generated singlet oxygen. Various conventional systems for chemical generation can be used including hydrogen peroxide and sodium hypochlorite, hydrogen peroxide and peracids in alkaline solution, or thermal decomposition of the ozone-triphenyl phosphite adduct. Oxidation of the enolate substrate is effected by contacting the substrate with one of the reagent systems listed above.

An N-substituted 3-O-alkylnoroxymorphone having the formula

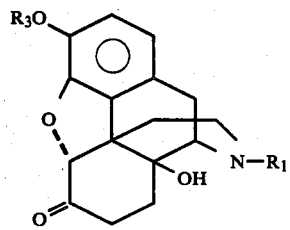

(Formula VI)

is prepared by catalytic hydrogenation of the compound of Formula V. It is believed that the compounds of Formula VI are also novel. Hydrogenation of the compounds of Formula V is typically carried out at a pressure of 1–10 atm. using a supported platinum metal catalyst, for example, 3–10% palladium on carbon, suspended in a solution of the compound of Formula V. Alcohols and alcohol/water mixtures are the preferred solvents for use in the hydrogenation step. Conventional catalyst concentration and temperatures can be used. Reaction takes place readily at 1 atm. using 50% by weight (substrate basis) of 10% Pd/C catalyst. However, for commercial operations, higher pressures and lower catalyst concentrations may be preferred. The product of Formula VI is recovered by filtering out the catalyst and evaporating solvent from the filtrate.

From the compound of Formula VI, noroxycodone or another 3-O-alkylnoroxymorphone having the structure

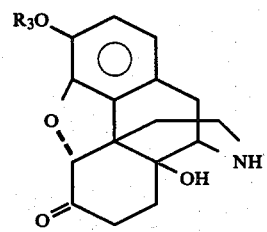

(Formula VII)

can be produced in one step and noroxymorphone

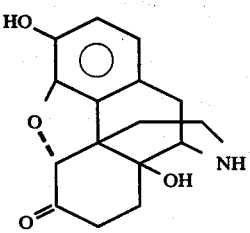

(Formula VIII)

can be produced in two.

To produce the compound of Formula VII, the compound of Formula VI is hydrolyzed with an acid in the presence of water. Preferably sulfuric acid is used, but other mineral acids are also effective. Acid concentrations in this step are conventional and non-critical. The reaction should be carried out at approximately atmospheric reflux temperature. After the hydrolysis is complete the product of Formula VII is recovered by neutralizing the acid solution with base and extracting the product with an appropriate solvent, such as chloroform.

To produce noroxymorphone (Formula VIII), the compound of Formula VI must be both O-dealkylated and hydrolyzed. Hydrolysis is carried out in the manner described above while O-dealkylation is accomplished by reaction with a Lewis acid such as boron tribromide or pyridinium chloride, the former being preferred. For reaction with BBr₃, halogenated solvents are preferred and the reaction is advantageously carried out at −20° to +25° C. The two steps for conversion of the compound of Formula VI to that of Formula VIII can be carried out in either sequence; i.e. either

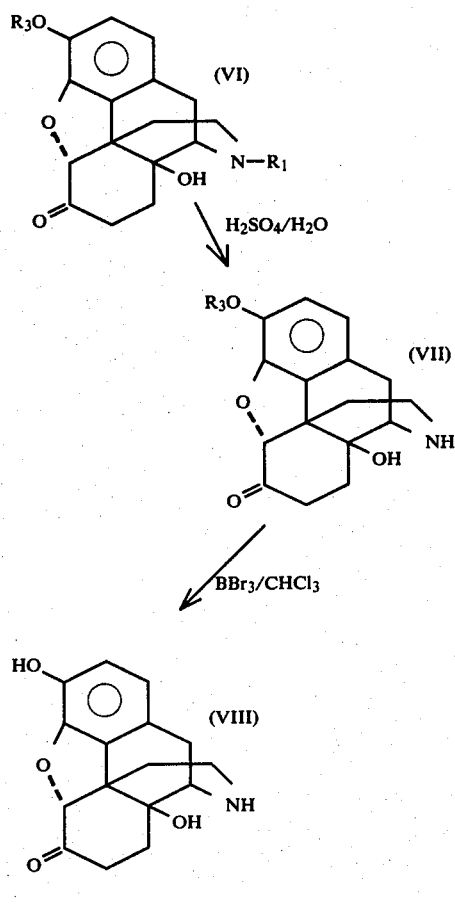

or:

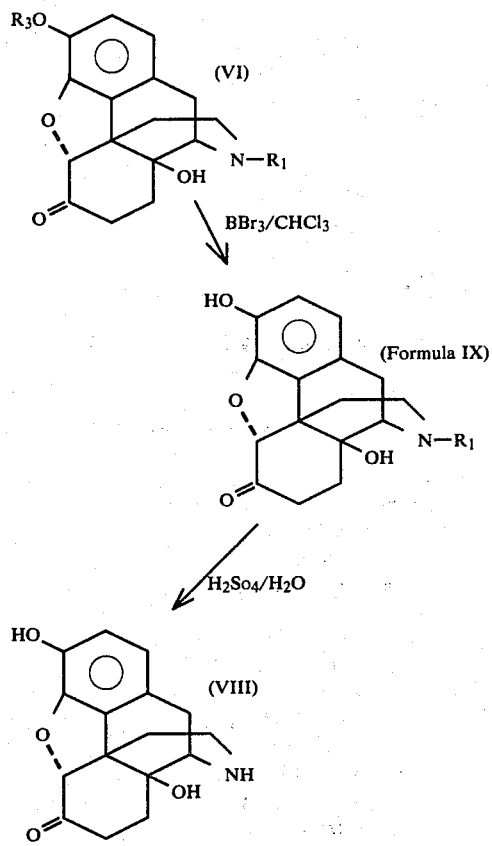

However, the latter route generally provides better yields and is preferred.

Each step of the synthesis route of invention is a reliable straightforward operation which does not require elaborate separations for recovery of reaction product. Moreover, as noted above, the first four steps of the overall synthesis (N-demethylation; oxidation to morphinone structure; formation of enolate; and singlet oxygen reaction to introduce the 14-hydroxy group) may be carried out without purification of intermediates. It is preferred that the N-substituted-3-O-alkylnormorphinone product of Formula III be recovered and dissolved in an acid anhydride such as acetic anhydride for the enolate (Formula IV) formation step. In any event, the process is subject to routine and effect process control to produce the 14-hydroxymorphinan precursors in high yield.

The following examples illustrate the invention.

EXAMPLE 1

A reaction mixture was prepared containing codeine (1.00 g; 3.34 millimoles; supplied by Mallinckrodt, Inc. of St. Louis, Mo.) ethyl chloroformate (1.90 ml.; 20.0 millimoles) and anhydrous potassium carbonate (0.386 g; 3.86 millimoles) in a chloroform solvent (100 ml.). The mixture was refluxed under nitrogen at atmospheric pressure for eight hours to effect reaction of the ethyl chloroformate and codeine. At the conclusion of the reaction, the solution was cooled, washed several times with water, dried over anhydrous sodium sulfate, and evaporated to yield 1.19 g (3.34 millimoles, 100%) N-ethoxycarbonylnorcodeine as a colorless oil. The structure of the product was confirmed by the following analyses: IR 2.81–3.04 9br), 5.97; NMR 6.66 (1, d, J=8.5, H-2), 6.55 (1, d, J=8.5, H-1), 5.74 (1, d, J=9.0, H-7), 5.27 (1, d, J=9.0, H-8), 4.86 (1, d, J=7.5, H-5), 4.14 (2, m, OCH$_2$CH$_3$), 3.82 (3, s, OMe), 1.26 (3, m, OCH$_2$CH$_3$); mass spectrum m/e 357 (M+, 68), 241 (100), 209 (95), 181 (32).

The crude N-ethoxycarbonylnorcodeine product was then dissolved in chloroform (500 ml), manganese dioxide (10 g) was mixed with the solution, and the resultant slurry was stirred at room temperature for ten minutes. Solids were then removed from the mixture by filtration through Celite and the filtrate evaporated to afford 1.10 grams of an oil. This crude product was purified by column chromatography using silica gel/15% water and a 50% chloroform/hexane eluent to yield N-ethoxycarbonylnorcodeinone (1.09 grams; 3.01 millimoles; 90%) as a colorless oil. Attempts to crystallize the oil were unsuccessful. The structure of the product was confirmed by the following analyses: IR 5.96μ; NMR 6.65 (1, d, J=9.0, H-2), 6.62 (1, d, J=10.0, H-8), 6.58 (1, d, J=9.0, H-1), 6.08 (1, d, J=10.0, H-7), 4.95 and 4,84 (1,br,s,H-9), 4.66 (1, s, H-5), 4.14 (2, m. OCH$_2$CH$_3$), 3,82 (3, s, OMe), 1.25 (3, m, OCH$_2$CH$_3$); mass spectrum m/e 355 (M+, 100), 266 (25), 251 (25), 240 (90), 239 (60), 225 (47), 211 (32); $^{13}$C NMR 193.71 (C-6), 155.37 (carbamate C=O), 146.88 (c-*0, 145.16 (C-4), 142.97 (C-3), 133.16 (C-7), 128, 12 (C-12), 124.93 (C-11), 120.47 (C-1), 116.00 (C-2), 87.88 (C-5), 61.69 (carbamate CH$_2$), 57.11 (c-3 OMe), 50.65 (C-9), 43.63 (C-13), 40.36 (C-14), 38.15 (C-16), 33.64 (C-15), 29.30 (C-10), 14.70 (carbamate CH$_3$); UV max (MeOH) 229 nm ($\epsilon$15,780), 282 (2127); [α]$_D$−280° (c 0.30). Anal. (C$_{20}$H$_{21}$NO$_5$) C, H, N.

A solution was prepared containing N-ethoxycarbonylnorcodeinone (100 mg; 0.282 millimoles) and fused anhydrous sodium acetate (10 mg.) in acetic anhydride (2 ml.). This solution was refluxed for 1.5 hours under nitrogen at atmospheric pressure. Thereafter, excess acetic anhydride was removed at 25° C. under high vacuum and the residue was diluted with water and extracted with chloroform to afford a brown oil (116 mg.). This crude product was purified by chromatography using a short column of silica gel/15% water and ether as an eluent to yield the dienol acetate of N-ethoxycarbonyl norcodeinone (97 mg; 0.244 millimoles; 80%) as a colorless oil. The structure of the product of this reaction step was confirmed by the following analyses: IR 5.70, 5.94; NMB (60 MHz) 6.67 (1, d, J=9.0, H-2), 6.51 (1, d, J=9.0, H-1), 5.69 (1, d, J=6.5, H-8), 5.52 (1, d, J=6.5, H-7), 5.44 (1, s, H-5), 5.27-4.94 (1 brs, H-9), 4.11 (2, m, OCH$_2$CH$_3$) 3.81 (3, s, OMe), 2.14 (3, s, OCOCH$_3$), 1.21 (3, m, OCH$_2$CH$_3$); mass spectrum m/e 397 (M+, 40), 355 (78), 326 (35), 266 (40), 254 (58), 253 (100).

A solution was prepared containing N-ethoxycarbonylnorcodeinone dienol acetate (97 mg.; 0.244 millimoles) and rose bengal (10 mg.) in a solvent comprising 10% methanol and 90% methylene chloride (50 ml.). This solution was entrained in oxygen and irradiated for one hour with two visible lamps (G.E. Quartzline, DWY 120 volts, 650 watts). During irradiation, the solution was maintained at 12° C. After irradiation of the solution, thiourea (100 mg.) was added thereto and the resultant mixture stirred for twelve hours to quench the peroxides formed in the singlet oxygen reaction. The solvents were thereafter evaporated to leave a residue which was dissolved in chloroform, washed with water, dried over sodium sulfate and evaporated to afford a crude product in the form of a red oil (113 mg.).

A major component of this oil was isolated by preparative thin layer chromatography (ether) to yield a yellow oil (63 mg, 0.17 millimoles, 71%) which crystallized from ethyl acetate/hexane. The crystallized product had a melting point of 154° to 155° C. and was identified as N-ethoxycarbonyl-14-hydroxynorcodeinone by the following analyses: IR 2.83–3.10 (br), 5.96μ; NMR 6.74 (1, br d, J=9.0, H-8), 6.71 (1, d, J=8.5, H-2), 6.61 (1, d, J=8.5, H-1), 6.14 (1, d, J=9.0, H-7), 4.72 (1, s, H-5), 4.18 (2, m, OCH$_2$CH$_3$), 3.85 (3, s, OMe), 1.33 (3, t, OCH$_2$CH$_3$); mass spectrum m/e 371 (M+, 100), 353 (47), 325 (35), 280 (45); $^{13}$C NMR 194.13 (C-6), 156.93 (carbamate C=O), 147.79 (C-8), 144.55 (C-4), 143.08 (C-3), 133.87 (C-7), 130.13 (C-12), 124.22 (C-11), 120.06 (C-1) 155.75 (C-2), 86,82 (C-5), 68.13 (C-14), 62.12 (carbamate CH$_2$), 56.96 (C-3 OMe), 55.90 (C-9), 47.32 (C-13), 37.60 (C-16), 31.61 (C-10), 27.57 (C-15), 14.60 (carbamate CH$_3$); [α]$_D$−201° (c 0.30). Anal. (C$_{20}$H$_{21}$NO$_6$) C, H, N.

EXAMPLE 2

N-ethoxycarbonyl-14-hydroxynorcodeinone was prepared in accordance with the synthesis route described in Example 1 but without purification of the intermediates. When codeine (1.00 g; 3.34 millimoles) was N-demethylated with ethyl chloroformate and oxidized with manganese dioxide as described in Example 1, 1.00 grams of crude N-ethoxycarbonylnorcodeinone was obtained. This intermediate was refluxed for 1.5 hours with sodium acetate (100 milligrams) in acetic anhydride (20 ml.) to yield the N-ethoxycarbonylnorcodeinone dienol acetate (1.27 g) as a dark brown gum. Reaction of the latter intermediate with singlet oxygen (100 mg. rose bengal in 500 ml. of 10% methanol/90% methylene chloride for 1.25 hours) afforded a red oil (1.40 g) which was purified by chromatography over silica gel/15% water using ether as an eluent to yield N-ethoxycarbonyl-14-hydroxynorcodeinone (0.81 grams; 2.2 millimoles; 66% overall from codeine) as a yellow orange oil, homogeneous to thin layer chromatography analysis, which crystallized as described in Example 1.

EXAMPLE 3

A solution was prepared containing N-ethoxycarbonyl 14-hydroxynorcodeinone (200 mg; 0.539 millimoles) in absolute ethanol (100 ml). A 10% palladium on carbon catalyst (100 mg) was slurried with the solution and hydrogen bubbled through the slurry with stirring for one hour. The suspension was filtered to remove the catalyst and the filtrate evaporated to yield N-ethoxycarbonylnoroxycodone (180 mg; 3.4 millimoles; 90%) as a clear oil which crystallized from methanol/ether. The crystallized product had a melting point of 113°–115° C. The N-ethoxycarbonylnoroxycodone structure was confirmed by the following instrumental analyses: IR 2.81–3.06 (br), 5.79, 5.95μ; NMR 6.72 (1, d, J=8.5, H-2), 6.62 (1, d, J=8.5, H-1), 4.65 (1, s, H-5), 4.19 (2, m, OCH$_2$CH$_3$), 3.89 (3, s, OMe), 1.30 (3, m, OCH$_2$CH$_3$); mass spectrum m/e 373 (M+, 100), 355 (20), 258 (40), 201 (58); [α]$_D$−317° (c 0.30); Anal. (C$_{20}$N$_{23}$NO$_6$) C, H, N.

EXAMPLE 4

A suspension comprising N-ethoxycarbonyl-noroxycodone as prepared in Example 3 (150 mg; 0.402 millimoles) in 5N sulfuric acid (5 ml) was refluxed under nitrogen at atmospheric pressure for twelve hours. The solution was cooled, made basic with solid sodium bicarbonate and extracted with chloroform to yield noroxycodone as a solid having a melting point of 170°–172° C. (literature value 174°–175° C.). The structure of the product was confirmed by the following analyses: IR 2.82–3.04 (br), 5.80; NMR 6.68 (1, d, J=8.5, H-2), 6.60 (1, d, J=8.5, H-1), 4.63 (1, s, H-5), 3.87 (3, s, OMe); mass spectrum m/e 301 (M+, 20), 145 (23), 117 (71), 103 (100), 101 (85); $[\alpha]_D-232°$ (c 0.20) (lit $[\alpha]_D-205°$, c 0.4). By comparison a sample of noroxycodone obtained from Mallinckrodt, Inc. exhibited mp 170°–173°; $[\alpha]_D^{26}-237°$ (c 0.20).

The hydrochloride salt of noroxycodone was prepared by adding saturated methanolic hydrogen chloride to a solution of noroxycodone in methanol. Subsequent addition of ether gave a precipitate which was crystallized from methanol/ether to give the hydrochloride which exhibited a melting point of 280°–283° C. and an elemental analysis of: ($C_{17}H_{20}NO_4Cl\cdot CH_3OH$) C,H,N.

In view of the above, it will be seen that the several objects of the invention are achieved and other advantageous results attained.

As various changes could be made in the above products and methods without departing from the scope of the invention, it is intended that all matter contained in the above description shall be interpreted as illustrative and not in a limiting sense.

I claim:

1. A process for producing an N-substituted 3-O-alkyl-14-hydroxynormorphinone derivative having the structural formula:

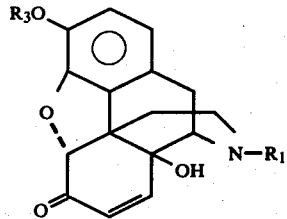

where $R_1$ is selected from the group consisting of

and cyano, $R_{11}$ being selected from the group consisting of aliphatic, aryl, oxyaliphatic and aryloxy substituents, and $R_3$ is lower alkyl, the process comprising:
contacting and reacting an N-substituted 3-O-alkylnormorphinone enolate substrate with singlet oxygen, said enolate substrate having the structural formula:

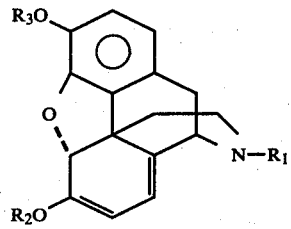

where $R_1$ and $R_3$ are as defined above and $R_2$ is an acyl group, whereby singlet oxygen reacts with the enolate substrate to substitute a hydroxyl group in the 14 position and the enolate structure is oxidized to a normorphinone structure.

2. A process as set forth in claim 1 wherein said enolate substrate is contacted with molecular oxygen in the presence of light and a sensitizing agent effective for forming singlet oxygen from molecular oxygen in the presence of light.

3. A process as set forth in claim 2 wherein said agent is selected from the group consisting of rose bengal, methylene blue, eosin, erythrosine, chlorophyll A, chlorophyll B, hematoporphyrin, and zinc tetraphenylporphin.

4. A process as set forth in claim 3 wherein said agent is rose bengal or methylene blue and said light comprises visible light.

5. A process as set forth in claim 1 wherein said enolate substrate is contacted with molecular oxygen in the presence of a reagent effective for chemically forming singlet oxygen from molecular oxygen.

6. A process as set forth in claim 1 wherein $R_1$ is

and $R_{11}$ is alkoxy.

7. A process as set forth in claim 6 wherein $R_{11}$ is ethoxy.

8. A process as set forth in claim 6 wherein $R_2$ is acetyl.

9. A process as set forth in claim 7 wherein said normorphinone enolate is prepared by reacting an N-substituted 3-O-alkylnormorphinone derivative having the structural formula

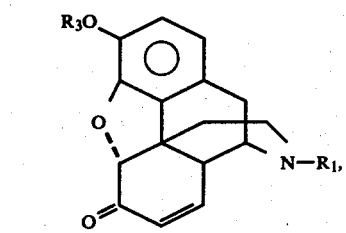

where $R_1$ and $R_3$ are as defined above, with an acid anhydride having the formula

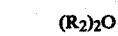

or an acyl halide having the formula

where X is a halogen and $R_2$ is as defined above, in the presence of a base.

10. A process as set forth in claim 9 wherein said normorphinone derivative is prepared by the steps of: reacting a 3-O-alkylmorphine with a cyanogen halide or a compound having the formula

where $R_{12}$ is oxyaliphatic or aryloxy and X is as defined above, in the presence of a weak base to produce an N-substituted 3-O-alkylnormorphine having the formula
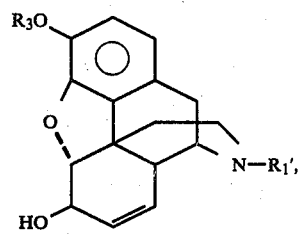
where $R_1'$ is selected from the group consisting of cyano and
and oxidizing said N-substituted 3-O-alkylnormorphine to produce said nonmorphinone derivative.
* * * * *